(12) United States Patent
Chang et al.

(10) Patent No.: US 11,648,382 B2
(45) Date of Patent: May 16, 2023

(54) MICRONEEDLE STRUCTURE AND MANUFACTURING METHOD AND MANUFACTURING APPARATUS FOR THE SAME

(71) Applicant: KOREA INSTITUTE OF MACHINERY & MATERIALS, Daejeon (KR)

(72) Inventors: Sunghwan Chang, Daejeon (KR); Jung Yup Kim, Daejeon (KR); Jaegu Kim, Daejeon (KR); Yeong-Eun Yoo, Daejeon (KR)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 581 days.

(21) Appl. No.: 16/642,464

(22) PCT Filed: Jul. 6, 2018

(86) PCT No.: PCT/KR2018/007712
§ 371 (c)(1),
(2) Date: Feb. 27, 2020

(87) PCT Pub. No.: WO2019/045254
PCT Pub. Date: Mar. 7, 2019

(65) Prior Publication Data
US 2020/0261708 A1    Aug. 20, 2020

(30) Foreign Application Priority Data

Aug. 30, 2017  (KR) .................. 10-2017-0110183

(51) Int. Cl.
*A61M 37/00* (2006.01)

(52) U.S. Cl.
CPC . *A61M 37/0015* (2013.01); *A61M 2037/0023* (2013.01); *A61M 2037/0038* (2013.01);
(Continued)

(58) Field of Classification Search
CPC ...... A61M 37/0015; A61M 2037/0023; A61M 2037/0038; A61M 2037/0046;
(Continued)

(56) References Cited

U.S. PATENT DOCUMENTS

2007/0255205 A1   11/2007  Griss et al.
2015/0306363 A1*  10/2015  Meyer ............... A61M 37/0015
                                                            604/173

FOREIGN PATENT DOCUMENTS

KR    1020160119679    10/2016
KR      101692266      1/2017
(Continued)

*Primary Examiner* — Amber R Stiles
(74) *Attorney, Agent, or Firm* — Lex IP Meister, PLLC

(57) ABSTRACT

A microneedle structure, a manufacturing method therefor, and a manufacturing apparatus therefor are presented. The microneedle structure manufacturing method according to one embodiment of the present invention comprises the steps of: a) injecting, into a lower mold comprising a microneedle intaglio, a polymer solution containing a biocompatible polymer; and b) coupling a shape control mold, which comprises a protrusion, to the lower mold such that one end of the protrusion of the shape control mold is impregnated with the biocompatible polymer solution injected into the microneedle intaglio.

15 Claims, 14 Drawing Sheets

(52) U.S. Cl.
CPC ............... *A61M 2037/0046* (2013.01); *A61M 2037/0053* (2013.01)

(58) Field of Classification Search
CPC ............. A61M 2037/0053; A61B 5/15; A61B 5/150984; B29C 39/00; B29C 39/02; B29C 39/26; B29C 39/026; B29C 39/003; B29C 39/028; B29K 2995/0056; B29L 2031/7544
See application file for complete search history.

(56) References Cited

FOREIGN PATENT DOCUMENTS

| | | |
|---|---|---|
| KR | 101728526 | 4/2017 |
| KR | 1020170061042 | 6/2017 |

\* cited by examiner

MICRONEEDLE STRUCTURE AND MANUFACTURING METHOD AND MANUFACTURING APPARATUS FOR THE SAME

TECHNICAL FIELD

The present invention relates to a microneedle structure, a method for manufacturing the microneedle, and a microneedle manufacturing apparatus, and more particularly, it relates to an implantable microneedle structure that can supply a precisely defined amount of a drug, while having excellent mechanical strength and being detachable in a short time, a manufacturing method of the microneedle structure, and a manufacturing apparatus of the microneedle structure.

BACKGROUND ART

A needle is used as a tool for collecting biological samples such as blood, tissues, and the like or injection of drugs into the body for the purpose of diagnosing a disease. A typically used needle is a macroneedle of which a diameter is in an order of millimeters. However, such a macroneedle leaves severe damage to the tissue when penetrating biological tissue barriers, causing serious pain in use.

Since a microneedle, which is a needle having a micrometer (μm) diameter does not leave any trauma when penetrating biological tissue barriers and does not cause pain, it a popular alternative to macroneedles and is expected to be widely used not only in the medical field but also in the cosmetic field.

In order to provide a painless and nontraumatic effect, the diameter of the microneedle should be adjusted to be tens to hundreds of micrometers, and the microneedle should have the strength and shape to withstand at least the biological barrier penetration pressure and an appropriate length for effective injection of a desired drug. In addition, in order to utilize such a microneedle in a wide range, manufacturing techniques that can easily produce microneedles in mass production and can reduce manufacturing cost by using a simple manufacturing process and a simple apparatus should be prepared.

Meanwhile, an implantable microneedle is formed of a biocompatible polymer material, and thus drugs are delivered as the microneedle is biodegraded after being injected into the skin. However, in case of the implantable microneedle, it takes several minutes to several months for dissolution and decomposition in the body. Thus, there is a problem that time to be applied to the skin is long, causing inconvenience in use, and furthermore, the drug may be removed before a fixed amount of drug is all injected.

In order to solve such a problem, a method in which centrifugation is carried out while injecting a polymer solution into the microneedle mold such that an air pocket is formed inside the microneedle and the air pocket is cut by a force, thereby separating a patch, may be used. However, when the air pocket is formed inside the needle by centrifugation, a side wall of the air pocket may not have a uniform thickness, and the thickness of the side wall of the air pocket is not easy to control such that the mechanical strength is significantly reduced, causing damage to the microneedle before or during the penetration of the skin barrier, and there is a problem in that it is impossible to control the location, arrangement, and shape of the air pocket to have strength that can withstand a biological barrier penetration pressure.

DISCLOSURE

Technical Problem

Exemplary embodiments of the present invention are made an effort to provide an implantable microneedle structure having excellent ease of use by shortening utilization time while having designed strength.

In addition, the exemplary embodiments of the present invention provide an implantable microneedle structure that can be cut in a short period of time by dissolution.

In addition, the exemplary embodiments of the present invention provide a microneedle structure that can inject a designed amount of drug, and can be detachable (cut) in very short period of time by being degradable not only by body fluids but also by an externally injected solvent.

Further, the exemplary embodiments of the present invention provide a manufacturing method that can manufacture an implantable microneedle structure having a designed strength and short utilization time using an inexpensive method capable of mass production simply in a short time.

Technical Solution

A microneedle structure manufacturing method according to an exemplary embodiment of the present invention includes: a) injecting a polymer solution containing a biocompatible polymer into a lower mold that includes a microneedle intaglio; and b) coupling a shape control mold to the lower mold to impregnate one end of a protrusion included in the shape control mold into the biocompatible polymer solution injected into the microneedle intaglio.

In the microneedle structure manufacturing method according to the exemplary embodiment of the present invention, the a) may include: a1) combining the upper mold including through-holes to be spaced apart from the upper portion of the lower mold, while disposing a penetration-type pore apart from an upper portion of the microneedle intaglio; and a2) injecting the polymer solution to fill at least a part of a separation space between the upper mold and the lower mold while filling the microneedle intaglio, and in the b), one end of the protrusion is impregnated into the biocompatible polymer solution filled in the microneedle intaglio through the penetration-type pore.

In the microneedle structure manufacturing method according to the exemplary embodiment of the present invention, the b) may satisfy Equation 1.

$$0.1 L_0 \leq P_{wiretip} \leq 0.9 L_0 \qquad \text{(Equation 1)}$$

In Equation 1, $L_0$ denotes a length of a microneedle intaglio, and $P_{wiretip}$ denotes a position of one end of the protrusion when the lowest point of the microneedle intaglio is zeroed.

In the microneedle structure manufacturing method according to the exemplary embodiment of the present invention, the shape control mold may further include a spacer that forms an empty space between the flat panel and the upper mold on a side that is the same as one side of the flat panel, in which the protrusion is located.

In the microneedle structure manufacturing method according to the exemplary embodiment of the present invention, the shape control mold may further include a flat panel, and in the b), a protrusion including one to twelve wires may be located only in an opening area, which is a flat panel area corresponding to an opening of the microneedle intaglio in the flat panel of the shape control mold.

In the microneedle structure manufacturing method according to the exemplary embodiment of the present invention, when the protrusion includes one wire, the wire is located at a center of the opening area, and when the protrusion includes two or more wires, the wires are located to satisfy Equation 2.

$$\theta=360°/n \quad \text{(Equation 2)}$$

Herein, θ denotes an angle (°) between two wires neighboring each other with reference to the center of the opening area, and n denotes a natural number from 2 to 12, which is the number of wires.

In the microneedle structure manufacturing method according to the exemplary embodiment of the present invention, the protrusion may include two or more wires, and neighboring wires may contact each other.

In the microneedle structure manufacturing method according to the exemplary embodiment of the present invention, the protrusion may include two or more wires, and the two or more wires may contact the edge of the opening area.

In the microneedle structure manufacturing method according to the exemplary embodiment of the present invention, the protrusion may satisfy Equation 3.

$$0.1 \leq A_{wire}/A_0 \leq 0.9 \quad \text{(Equation 3)}$$

(In Equation 3, $A_{wire}$ denotes a total area of all wire cross-sections included in a protrusion, and $A_0$ denotes the area of an opening area).

In the microneedle structure manufacturing method according to the exemplary embodiment of the present invention, the a2) may include: a2-1) injecting a first polymer solution that contains a first biocompatible polymer and a drug into the microneedle intaglio, while locating a liquid level of the first polymer solution in a lower portion of the $P_{wiretip}$; and a2-2) injecting a second polymer solution that contains a second biocompatible polymer to fill a space of the microneedle intaglio above the liquid level of the first polymer solution.

In the microneedle structure manufacturing method according to the exemplary embodiment of the present invention, the lower mold may include an intaglio array where two or more microneedle intaglios are arranged at a distance from each other, the shape control mold may include an array of wire-shaped protrusions corresponding to the intaglio array, and the upper mold may include an array of penetration-type pores corresponding to the intaglio array.

The microneedle structure manufacturing method according to the exemplary embodiment of the present invention may further include a separation mold that is located between the lower mold and the upper mold for separation therebetween, and the separation mold may have a shape that corresponds to an edge shape of the designed microneedle structure.

According to the microneedle structure manufacturing method according to the exemplary embodiment of the present invention, the same lower mold, the same upper mold, and the same shape control mold are used, while differentiating a separation mold such that a microneedle structure for a microneedle patch, having a different shape and a different size can be manufactured.

The microneedle structure manufacturing method according to the exemplary embodiment of the present invention may further include, after the b), curing the polymer solution and removing a mold that includes the lower mold and the shape control mold.

In the microneedle structure manufacturing method according to the exemplary embodiment of the present invention, a hydrophobic coating layer may be formed on an intaglio surface of the lower mold.

In the microneedle structure manufacturing method according to the exemplary embodiment of the present invention, the lower mold may include a first lower mold that includes a first intaglio area that corresponds to a tip of the microneedle and a second lower mold that includes a second intaglio area that corresponds to a pillar of the microneedle that includes a base portion of the microneedle.

The present invention includes a microneedle structure manufactured by using the above-described manufacturing method.

The present invention includes a microneedle structure manufacturing apparatus, and the microneedle structure manufacturing apparatus may be an apparatus used in the above-described manufacturing method.

A microneedle structure manufacturing apparatus according to the present invention includes: a lower mold that includes microneedle intaglio; a shape control mold that includes a protrusion, and is coupled with the lower mold to impregnate one end of the protrusion into the microneedle intaglio; and an injection portion that injects a polymer solution into the microneedle intaglio of the lower mold.

In the microneedle structure manufacturing apparatus according to an exemplary embodiment of the present invention, the shape control mold may further include a flat panel, and the protrusion may include one to twelve wires that are located in an opening area, which is a flat area corresponding to an opening of the microneedle, and when the protrusion includes one wire, the protrusion may be located at a center of the opening area, while when the protrusion includes two or more wires, Equation 2 may be satisfied:

$$\theta=360°/n \quad \text{(Equation 2)}$$

wherein θ denotes an angle (°) between two wires neighboring each other with reference to the center of the opening area, and n denotes a natural number from 2 to 12, which is the number of wires.

In the microneedle structure manufacturing apparatus according to an exemplary embodiment of the present invention, the protrusion may include two or more wires, and the two or more wires may contact the edge of the opening area or neighboring wires contact each other.

In the microneedle structure manufacturing apparatus according to an exemplary embodiment of the present invention, the protrusion may satisfy Equation 3:

$$0.1 \leq A_{wire}/A_0 \leq 0.9 \quad \text{(Equation 2)}$$

wherein $A_{wire}$ denotes a total area of all wire cross-sections included in a protrusion, and $A_0$ denotes the area of an opening area.

The microneedle structure manufacturing apparatus according to the exemplary embodiment of the present invention may further include an upper mold where a penetration-type pore is formed, wherein the upper mold may be coupled with the lower mold such that the penetration-type pore is located above the opening of the microneedle intaglio, and the shape control mold may further include a spacer that forms an empty space between the flat panel and the upper mold on a side that is the same as one side of the flat plane where the protrusion is located.

The microneedle structure manufacturing apparatus according to the exemplary embodiment of the present invention may further include a separation mold that separates the upper mold and the lower mold while being disposed between the lower mold and the upper mold.

In the microneedle structure manufacturing apparatus according to the exemplary embodiment of the present invention, a hydrophobic coating layer may be formed on an intaglio surface of the lower mold.

In the microneedle structure manufacturing apparatus according to the exemplary embodiment of the present invention, the lower mold may include a first lower mold that includes a first intaglio area that corresponds to a tip of the microneedle and a second lower mold that includes a second intaglio area that corresponds to a pillar of a microneedle that includes a base portion of the microneedle.

The present invention includes a microneedle structure.

A microneedle structure according to the present invention includes: a base layer, which is a flat layer; and a microneedle that is formed of a biocompatible polymer material and located on one side of the base layer, wherein the microneedle includes a pore that extends in a direction of the tip of the microneedle while penetrating the base layer such that one end of the pore is located inside the microneedle.

In the microneedle structure according to the present invention, the microneedle may include one wire-shaped pore, and the wire-shaped pore may have a concentric structure with respect to a central axis of a length direction of the microneedle.

In the microneedle structure according to the present invention, the microneedle may include two to twelve wire-shaped pores, and the wire-shaped pores may be arranged to surround a central axis of a length direction of the microneedle.

In the microneedle structure according to the present invention, the wire-shaped pores that are adjacent to each other may communicate with each other while being in contact with each other.

In the microneedle structure according to the present invention, the wire-shaped pore may contact the surface of the microneedle such that the wire-shaped pore and the outside of the microneedle communicate with each other.

In the microneedle structure according to the present invention, the wire-shaped pore may satisfy Equation 4:

$$0.1L_1 \leq E_{tip} \leq 0.9L_1 \quad \text{(Equation 2)}$$

wherein $L_1$ denotes a length of the microneedle, and $E_{tip}$ denotes a position of one end of the wire-shaped pore while zeroing the tip of the microneedle.

In the microneedle structure according to the present invention, the microneedle may satisfy Equation 5.

$$0.1 \leq A_{empty}/A_1 \leq 0.9 \quad \text{(Equation 2)}$$

wherein $A_{empty}$ denotes a total empty space area of cross-sections of all wire-shaped pores included in a microneedle, and $A_1$ denotes a cross-section of the microneedle.

In the microneedle structure according to the present invention, a first area, which is an area from the tip of the microneedle to below one end of the wire-shaped pore, may contain a first biocompatible polymer and a biochemical material, and other areas excluding the first area in the microneedle may contain a second biocompatible polymer.

The present invention includes a patch that includes the above-described microneedle structure.

ADVANTAGEOUS EFFECTS

The manufacturing method of the microneedle structure according to the exemplary embodiments of the present invention can manufacture a microneedle structure where a wire-type pore having a designed shape and a designed size is formed at a designed position by a wire-shaped protrusion of a shape control mold, and accordingly, the microneedle is cut by dissolution or decomposition of a wall of the wire-type pore, thereby significantly reducing utilization time while providing a designed strength.

In addition, since wires that form a wire-shaped protrusion are regularly arranged to surround a center of the microneedle intaglio, a support axis (material axis) that endures and supports external force is formed in a central axis of the needle, which reaches from the tip of the microneedle to the base portion of the microneedle, thereby providing excellent physical strength while shortening utilization time by the wire-shaped pore.

In addition, as the wire-shaped pore is formed by inserting the wire-shaped protrusion of the shape control mold into a predetermined location in the microneedle through a base layer that connects two or more microneedles, an opening that communicates with the wire-type pore of the microneedle may be formed in the base layer. Such an opening may serve as an inlet of a solvent of a biocompatible polymer during use of the microneedle structure, thereby further shortening the utilization time.

In addition, since the microneedle is cut in an area that is defined as an area between the end of the wire-shaped protrusion in the microneedle intaglio and an opening (i.e., the opening of the lower mold) of the microneedle intaglio in the mold, a cutting position can be precisely controlled. Since the cutting position is controllable, a drug can be controlled to be contained only in an area where the microneedle is not cut, and thus a precisely defined amount of drug can be accurately injected.

In addition, two or more polymer solutions are sequentially injected into the microneedle intaglio of the mold such that biostability can be maximized while improving the cutting speed of the microneedle (decomposition or dissolution speed of the wire-shaped pore wall).

In addition, as the microneedle is manufactured by injecting and curing a polymer solution into a mold, the manufacturing process becomes simple, and not only inexpensive mass production but also large area production can be enabled.

The microneedle structure according to the exemplary embodiments of the present invention can be easily manufactured in a form of a mask pack, a small-sized band-type patch, and the like, and when additional treatments for increasing the local temperature of the skin, such as a pack or infrared irradiation, are performed after the patch is attached to the skin, and then compared to the general microneedle in order to improve the deliverability of the drug inserted into the living body or to relieve pain, the drug can be effectively delivered due to the effect of having improved biosolubility compared to a general microneedle.

MODE FOR INVENTION

Figure 1:
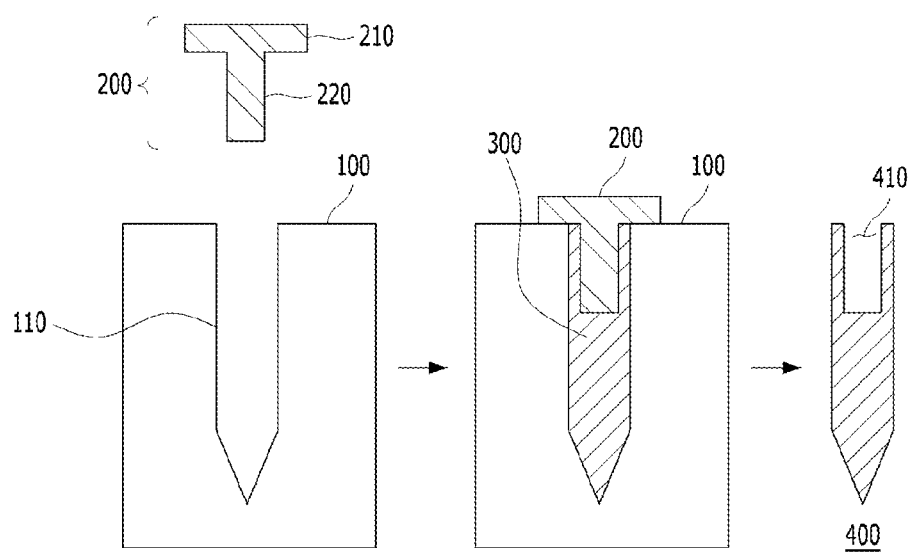
FIG. 1 is a process diagram of a manufacturing process of a microneedle structure according to an exemplary embodiment of the present invention.

The present invention will be described more fully hereinafter with reference to the accompanying drawings, in which exemplary embodiments of the invention are shown.

As those skilled in the art would realize, the described embodiments may be modified in various different ways, all without departing from the spirit or scope of the present invention. The drawings and description are to be regarded as illustrative in nature and not restrictive. Like reference numerals designate like elements throughout the specification.

In this specification, duplicate descriptions of the same constituent elements are omitted.

Further, in the present specification, it is to be understood that when one component is referred to as being "connected to" another component, it may be connected directly to another component or be connected to another component with a further component interposed therebetween. On the other hand, in the present specification, it is to be understood that when one component is referred to as being "directly connected to" another component, it may be connected to another component without the other component interposed therebetween.

In addition, terms used in the present specification are used only in order to describe specific exemplary embodiments, rather than limiting the present invention.

Further, in the present specification, singular forms are intended to include plural forms unless the context clearly indicates otherwise.

It should be further understood that terms "include" or "have" used in the present specification specify the presence of features, numerals, steps, operations, components, parts mentioned in the present specification, or combinations thereof, but do not preclude the presence or addition of one or more other features, numerals, steps, operations, components, parts, or combinations thereof.

Further, in the present specification, a term "and/or" includes a combination of a plurality of stated items or any one of the plurality of stated items. In the present specification, "A or B" may include "A", "B", or "all of A and B".

A manufacturing method of a microneedle structure according to the present invention includes a) injecting a polymer solution containing a biocompatible polymer into a lower mold including a microneedle intaglio, and b) combining a shape control mold so that one end of a wire-shaped protrusion of the shape control mold is impregnated into the biocompatible polymer solution injected into the microneedle intaglio.

According to the above-stated manufacturing method, a microneedle of a biocompatible polymer material can be manufactured by the lower mold, and at the same time, a microneedle structure where a wire-shaped pore having a designed shape and a designed size is formed at designed positions, can be manufactured.

In addition, the strength of the microneedle can be controlled by adjusting a shape, a size, a number, and/or an alignment of the wire included in the wire-shaped protrusion, and the microneedle having designed strength can be manufactured.

Accordingly, the microneedle structure can be cut in a short period of time by dissolution of an area where a wire-shaped pore is located, while having stable strength that is strong enough to not be destroyed by biological barrier penetration pressure.

Specifically, the manufactured microneedle structure has a designed strength that can withstand a biological tissues penetration pressure, but has a wire-shaped pore by the wire-type protrusion of the shape control mold, and thus the microneedle structure can be promptly cut by dissolution or decomposition of a pore wall of the wire-shaped pore, while being used.

Further, since the wire-shaped protrusion is inserted through an opening of the microneedle intaglio of the lower mold, a microneedle structure having a structure in which the wire-shaped pore penetrates a base portion of the microneedle can be manufactured.

The microneedle structure can be supplied with a solvent that dissolves or decomposes the biocompatible polymer from the outside through a wire-shaped pore that penetrates the base portion even when attached to an attachment target, thereby shortening utilization time.

In addition, the coupling of the polymer solution and the mold, which is a method that is extremely simple and easy, provides excellent reproducibility, and enables large-scale manufacturing, and enables manufacturing of a user-friendly microneedle structure having excellent detachability.

Accordingly, the microneedle structure of the present invention can be easily manufactured in a form of a mask pack, a small-sized band-type patch, and the like, and when additional treatments for increasing the local temperature of the skin, such as a pack or infrared irradiation, are performed after the patch is attached to the skin, and then compared to the general microneedle in order to improve the deliverability of the drug inserted into the living body or to relieve pain, the drug can be effectively delivered due to the effect of having improved biosolubility compared to a general microneedle.

FIG. 1 shows a process diagram of a manufacturing process of a microneedle structure according to an exemplary embodiment of the present invention.

As shown in the process diagram of FIG. 1, a lower mold 100 may include a microneedle intaglio 110. A shape control mold 200 may include a flat panel 210 and a wire-shaped protrusion 220 located on one side of the flat panel 210. A polymer solution 300 containing a biocompatible polymer may be injected into the intaglio 110 of the lower mold 100. After injection of the polymer solution 300, the control mold 200 may be combined to the lower mold 100 such that one end of the wire-shaped protrusion 220 can be soaked into the injected polymer solution. Next, the injected polymer solution 300 is cured and a mold including the lower mold 100 and the shape control mold 200 is removed such that a microneedle structure 4000 where a wire-shaped pore 410 is formed at a designed position with a designed shape and a designed size can be manufactured.

The biocompatible polymer may contain biodegradable polymers, biosoluble polymers, or mixtures thereof, and the polymer solution 300 may mean a solution in which the biocompatible polymer is dissolved in a solvent. The solvent of the polymer solution 300 may be any solvent known to dissolve the biocompatible polymer. As a detailed example, the solvent may be an aqueous solvent such as water or a polar organic solvent, but is not limited.

The biodegradable polymer may imply a polymer that is biocompatible and can be decomposed by body fluids, enzymes, and the like. As a specific and non-limiting example, the biodegradable polymer may include poly (lactide), poly (glycolide), poly (lactide-co-glycolide), polyanhydride, polyorthoester, polyetherester, polycaprolactone, polyesteramide, poly(butyric acid), poly(valeric acid), polyurethane, or copolymers or a mixture thereof, but this is not restrictive.

The biosoluble polymer may imply a water-soluble polymer having biocompatibility. As a specific and non-limiting example, the biosoluble polymer may include gelatin, pectin, dextran, hyaluronic acid or salts thereof, collagen, agar, arabic gum, xanthan gum, acacia gum, karaya gum, tragacanth gum, guar gum, carrageic acid, alginic acid, alginic acid salts (e.g., sodium alginate), methyl cellulose, ethyl cellulose, hydroxy ethyl cellulose, sodium carboxymethyl cellulose, soluble starch, pullulan, dextrin, carboxymethyl starch, dialdehyde starch, polyvinyl alcohol, polyvinylpyrrolidone, polyvinyl metacryl latex, polyacryl acid and salts thereof, a polyethylene oxide, a polypropylene oxide, a polyethylene oxide, a polypropylene oxide copolymer, a carboxyl-containing acryl resin, a carboxyl-containing polyester resin, water-soluble polyamide, water-soluble polyurethane, maltodextrin, polydextrose, or a mixture thereof, but this is not restrictive.

The microneedle intaglio 110 of the lower mold 100 may be a microneedle-shape intaglio having a sharp end while having a diameter and a length that are designed to be appropriate to its use.

As a practical example considering the use of an implantable microneedle for drug injection, a minor diameter of the microneedle intaglio 110 may be 10 μm to 500 μm and a length may be 200 μm to 3000 μm, but is not limited.

After the polymer solution 300 is injected into the microneedle intaglio 110 of the lower mold 100, the shape control mold 200 may be combined to impregnate one end of the wire-shaped protrusion 220 into the injected polymer solution 300.

A shape, a size, and an alignment of a wire-shape pore of the manufactured microneedle can be adjusted by a shape, a size, and an alignment of the wire-shaped protrusion 220 of a shape control mold 200, and a microneedle structure having a designed strength and a designed utilization time (microneedle cutting time by dissolution or decomposition) can be manufactured by simply changing the design of the wire-shaped protrusion.

After the shape control mold 200 is combined, the injected polymer solution 300 may be cured, and in the case, the curing may imply solidification by volatilization removal of the solvent. If necessary, heating for curing the injected polymer solution may be performed, and heating may be performed in a range that does not cause thermal damage to the biodegradable polymer.

After the injected polymer solution 300 is cured, the mold including the lower mold 100 and the shape control mold 200 is removed such that a microneedle 400 where the wire pore 410 having the designed size and the designed shape is formed at the designed position with the designed alignment can be manufactured.

Figure 2:
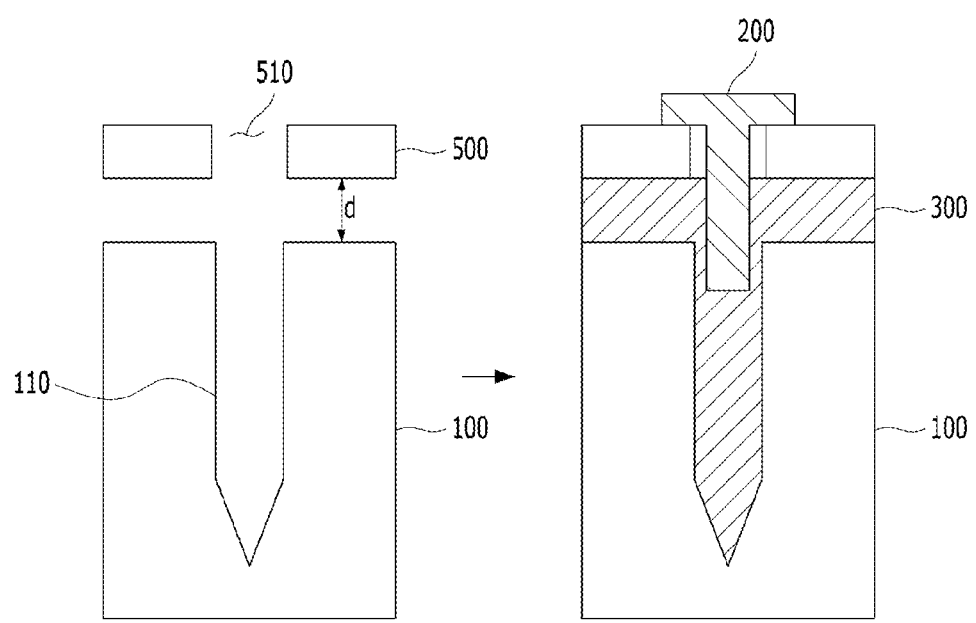
FIG. 2 is another process diagram of the manufacturing process of a microneedle structure according to the exemplary embodiment of the present invention.

FIG. 2 is another process diagram of the manufacturing process of a microneedle structure according to the exemplary embodiment of the present invention.

As shown in the example of FIG. 2, a) may include a1) combining the upper mold 500 including a penetration-type pore 510 and the lower mold 100 so as to locate the penetration-type pore 510 at a distance above the microneedle intaglio 110, and a2) injecting the polymer solution 300 to fill at least a part of a separation space d between the upper mold and the lower mold 100 while filling the microneedle intaglio 110.

When the upper mold 500 is used, in the step b), the shape control mold 200 may be combined such that one end of the wire-shaped protrusion 220 may be impregnated in the polymer solution 300 filled in the microneedle intaglio 110 through the penetration-type pore 510.

The penetration-type pore 510 of the upper mold 500 may have any size and any shape as long as at least an opening portion of the microneedle intaglio 110 is not covered by the upper mold 500. As a non-limiting example, the penetration-type pore 510 of the upper mold 500 may have a shape corresponding to the opening portion of the microneedle intaglio 110 and a size over the opening portion of the microneedle intaglio 110.

Such an upper mold 500 is advantageous in manufacturing of a microneedle array where two or more microneedles are arranged. Specifically, as the polymer solution 300 in injected to fill at least a part of the separation space d between the upper mold 500 and the lower mold 100, a microneedle structure 4000 including a base layer 430 that is formed of a biocompatible polymer material and connects base portions between two or more microneedles can be manufactured.

In addition, as shown in the process diagram of FIG. 2, after the upper mold 500 and the lower mold 100 are combined, the wire-shaped protrusion 220 of the shape control mold 200 may be inserted through the penetration-type pore 510 of the upper mold 500.

Accordingly, the manufactured microneedle structure 4000 may have a wire-shaped pore 410 opened out through the base layer 430, rather than a pore trapped inside the microneedle.

The base layer 430 remains exposed to the outside even when the microneedle structure 4000 is used. Accordingly, it should be noted that the fact that the wire-shaped pore 410 is opened to the outside means maintaining the open pore state even during the actual use of the microneedle structure 4000.

The wire-shaped pore 410 that maintains the state of being opened to the outside in use may also be dissolved by the solvent of the biocompatible polymer, injected from the outside through the wire-shaped pore 410 that maintains the open state, together with decomposition or dissolution in a living body. Therefore, even if a microneedle structure has a wire-shaped pore 410 formed of the same material and the same pore wall thickness, dissolution or dissolution speed can be significantly improved.

FIG. 1 and FIG. 2 illustrate an example in which the wire-shaped protrusion 220 is provided as a single wire. However, it is a matter of course that the present invention is not limited to the wire-like protrusion 220 made of a single wire, and the wire-shaped protrusion 220 may have various wire sizes, various shapes of wires, various numbers of wires and/or arrangements of wires in consideration of the size, formation, number, and arrangement of pores to be formed in the microneedle.

Based on the short axis of the wire included in the wire-shaped protrusion 220, the wire may have various shapes such as various polygons including a circle, an ellipse, a triangle, or an octagon, but, advantageously, it may have a shape corresponding to the shape of the cross-section perpendicular to the length direction of the microneedle intaglio.

Specifically, the shape of the cross-section of the microneedle intaglio may be polygonal such as a circle, an ellipse, a triangle, an octagon, and the like, and the minor cross-section of the wire included in the wire-shaped protrusion 220 corresponds to the shape of the cross-section of the microneedle intaglio.

More advantageously, the shape of the cross-section of the microneedle intaglio may be circular in terms of minimizing the penetration pressure while avoiding concentration of pressure, and accordingly, the minor cross-section of the wire may also be circular.

A length of the wire may be designed in consideration of a depth of the microneedle intaglio. Specifically, the wire-shaped protrusion inserted into the microneedle intaglio where the polymer solution in injected in step b) may satisfy Equation 1, and the wire of the wire-shaped protrusion may have a length that can satisfy Equation 1 in consideration of a length of the separation space or a thickness of the upper mold 500.

$$0.1L_0 \leq P_{wiretip} \leq 0.9L_0 \quad \text{(Equation 1)}$$

In Equation 1, $L_0$ denotes a length of the microneedle intaglio (i.e., a length from the base portion to the tip of the microneedle), and $P_{wiretip}$ denotes a position of one end of the protrusion while zeroing the lowest point of the microneedle intaglio.

Figure 3:
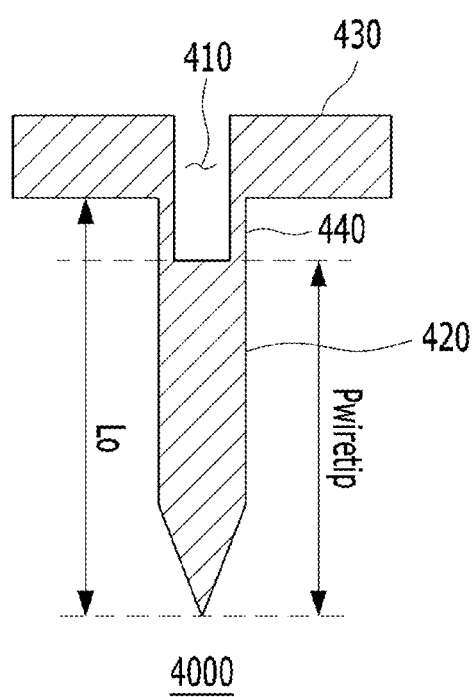
FIG. 3 is a cross-sectional view of a cross-section of a microneedle structure manufactured by a manufacturing method according to an exemplary embodiment of the present invention.

As shown in FIG. 3, a microneedle structure 4000 in which the base portion of the microneedle 420 is bound to the base layer 430, which is a flat layer, may be manufactured. Equation 1 implies that a distance from the tip of the microneedle 420 to the end of the wire-shaped pore 410 is $0.1L_0$ to 0.94 in the manufactured microneedle structure 4000.

Equation 1 indicates a condition that the microneedle can be cut in a specific narrow area while the pore wall 440 contacts the body fluid, and can be stably cut in a short time by dissolution or decomposition.

Specifically, the location of $P_{wiretip}$ given by Equation 1 is a condition that, when the microneedle is injected into a human body, a microneedle area at a specific portion is cut while a pore wall 440 of the wire-shaped pore 410 stably contacts the body fluid such that the designed microneedle area can maintain a state of being fully inserted into the human body.

In such an aspect, more advantageously, $0.5L_0 \leq P_{wiretip} \leq 0.7L_0$ can be satisfied. As a practical example, the length $L_0$ of the microneedle of the microneedle structure may be 10 μm to 2000 μm, more substantially 50 μm to 500 μm, but the present invention is not limited by the length of the microneedle.

The wire-shaped protrusion of the shape control mold may include one to twelve wires. Specifically, in the shape control mold, the protrusion including one to twelve wires may be located in an opening area, which is a flat area that corresponds to the opening of the microneedle intaglio in the lower mold, while having the same shape as the opening.

When the wire-shaped protrusion includes two or more wires, uniform strength in a radial direction of the manufactured microneedle can be assured, and, in order to secure a support axis (an axis of material) capable of supporting physical force from the microneedle tip to the base portion, it is advantageous that the wires are arranged regularly so as to surround the center of the opening region.

Figure 4:
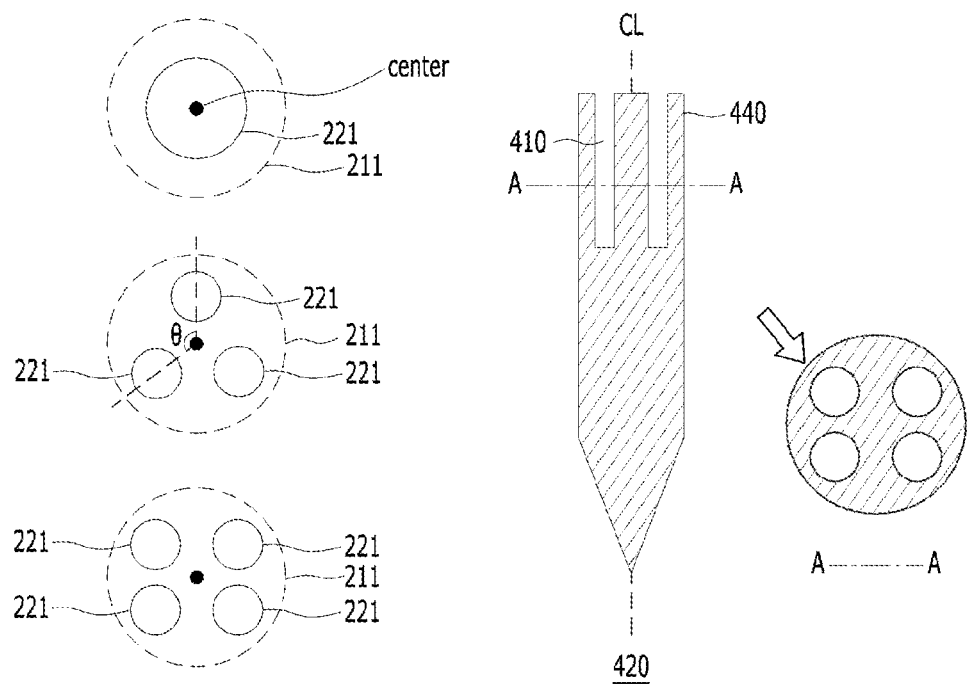
FIG. 4 is a bird's eye view of the shape control mold in a protrusion direction of the wire-shaped protrusion in the manufacturing method according to the exemplary embodiment of the present invention, and shows examples including one, three, and four wires.

FIG. 4 is a bird's eye view of the shape control mold 200 in a protrusion direction of the wire-shaped protrusion 220, and shows examples including one, three, or four wires 221. In FIG. 4, the dot-lined area implies an opening area 211, which is an area of the flat panel 210, and has the same shape as the opening of the microneedle intaglio of the lower mold while corresponding to the opening of the microneedle intaglio. In addition, each opening area 211 may correspond to each microneedle intaglio formed in the lower mold.

As shown in the example of FIG. 4, when a wire-shaped protrusion includes one wire 221, the wire 221 may be located at a center of the opening area 211. Thus, a portion where the wire-shaped pore is located in the microneedle may be formed in the shape of a hollow tube having a uniform wall thickness. The hollow tube having a uniform wall thickness has excellent physical and mechanical stability, and the microneedle can be cut and the utilization time can be significantly reduced by dissolving or decomposing the biocompatible polymer that forms the wall of the tube.

When the wire-shaped protrusion includes two or more wires 221, the two or more wires 221 may satisfy Equation 2. That is, when the wire-shaped protrusion includes two or more wires 221, the wires 221 may be regularly located to surround the center of the opening area 211.

$$\theta = 360°/n \quad \text{(Equation 2)}$$

Herein, θ denotes an angle (°) between two wires that neighbor each other with reference to the center of the opening area, and n denotes a natural number of 2 to 12, which is the number of wires included in the protrusion. In this case, the angle between two neighboring wires is an angle between two line segments that connect centers of the respective wires 221 and the center of the opening area 211.

For example, as shown in FIG. 4, when the number of wires is 3, an angle between neighboring wires may be 120°, and when the number is 4, the angle may be 90°.

Since the wire 221 is located to surround the center of the opening area 211, a material axis that can support physical force from the tip of the microneedle to the base portion can be formed, and when the microneedle structure is used, the microneedle can be prevented from breaking (cutting) during the attachment process due to local concentration of external forces such as penetration pressure in some regions.

Specifically, wires 221 are regularly located to surround a center of the opening area 211 as shown in the cross-sectional view of FIG. 4, which illustrates the microneedle 420 manufactured by using a shape control mold where a wire-shaped protrusion having four wires is formed, around the center of opening region 211, and thus a material axis that can endure external force may be formed at a central axis CL that connects a center of the base portion of the microneedle 420 and the tip of the microneedle 420.

In addition, a thickness of a wall between the surface of the microneedle 420 and the wire-shaped pore 410 may vary depending on positions. Accordingly, the wall surface portion (shown as the arrow in the A-A cross-section) having the thinnest thickness is preferentially dissolved or decomposed such that the wire-shaped pore 410 can communicate with the inside the body. The inside of the wire-shaped pore 410 is filled with the body fluid through such communication, and dissolution or decomposition with respect to wall surfaces of the rest of the wire-shaped pore 410 can be significantly quickly removed.

In addition, as shown in the example of FIG. 4, since the wire 221 is located to surround the center of the opening area 211, a material axis CL is formed in the length direction of the microneedle from the microneedle base portion to the tip of the microneedle, and material axes in the length direction of the microneedle may be regularly formed in an area where a wall surface between the surface of the microneedle 420 and the wire-shaped pore 410 is relatively thick. Such a material axis may serve as a support axis that endure external force generated during biological barrier penetration to thereby prevent the microneedle from being broken due to the external force.

When the wire-shaped protrusion includes two or more wires in the example of FIG. 4, the respective wires do not contact each other and they are separated by a constant distance from an edge of the opening area 211, but the present invention is not limited thereto.

Figure 5:
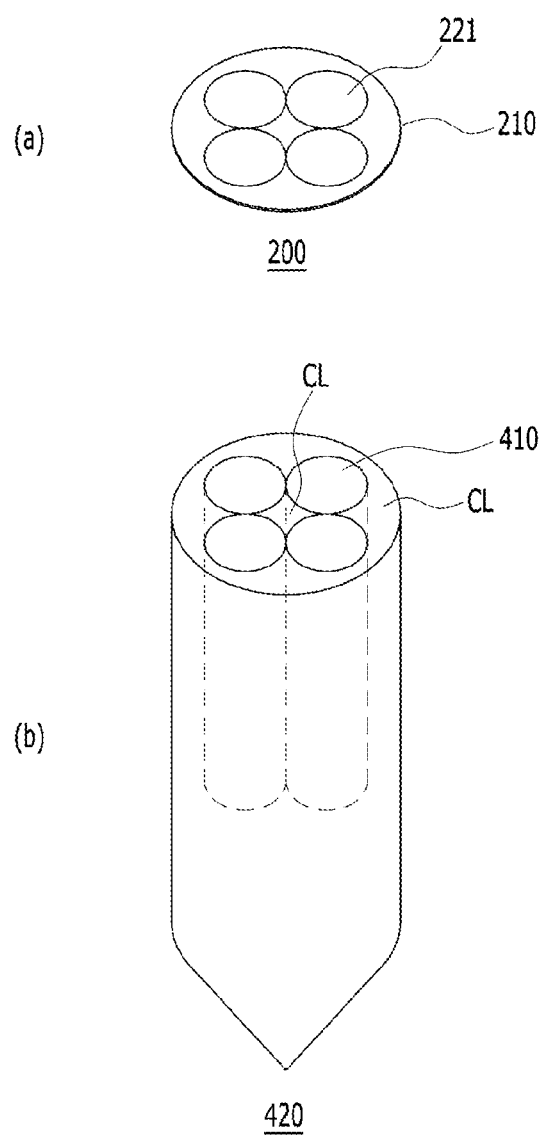
FIG. 5 is a bird's eye view of a shape control mold where a wire-shaped protrusion having four wires is formed in the manufacturing method according to the exemplary embodiment of the present invention, and a cross-sectional view of a microneedle manufactured by using the same.

Specifically, as shown in the example of FIG. 5, when the wire-shaped protrusion includes two or more wires, neighboring wires may contact each other.

Specifically, FIG. 5(a) is a bird's eye view of an example of when the wire-shaped protrusion includes four wires 221, the shape control mold 200 is viewed from the protrusion direction of the wires 221, and illustrates an example in which each of the four wires 221 contacts a wire 221 adjacent thereto.

Thus, as shown in 5(b), in the microneedle 420, a portion where the wire-shaped pore 410 is located has a material axis CL at a center of the microneedle 420, and a material axis CL of a surface layer that forms a closed loop that is separated by a constant distance from the material axis CL at the center may be formed.

The microneedle structure having the structure shown in FIG. 5(b) can assure strength that can endure an external force by the material axis CL at the center and the material axis CL of the surface layer, and even when any one portion in a wall surface of the wire-shaped pore is dissolved or degraded, all wire-shaped pores can be filled with the body fluid such that the microneedle can be more promptly cut.

Figure 6:
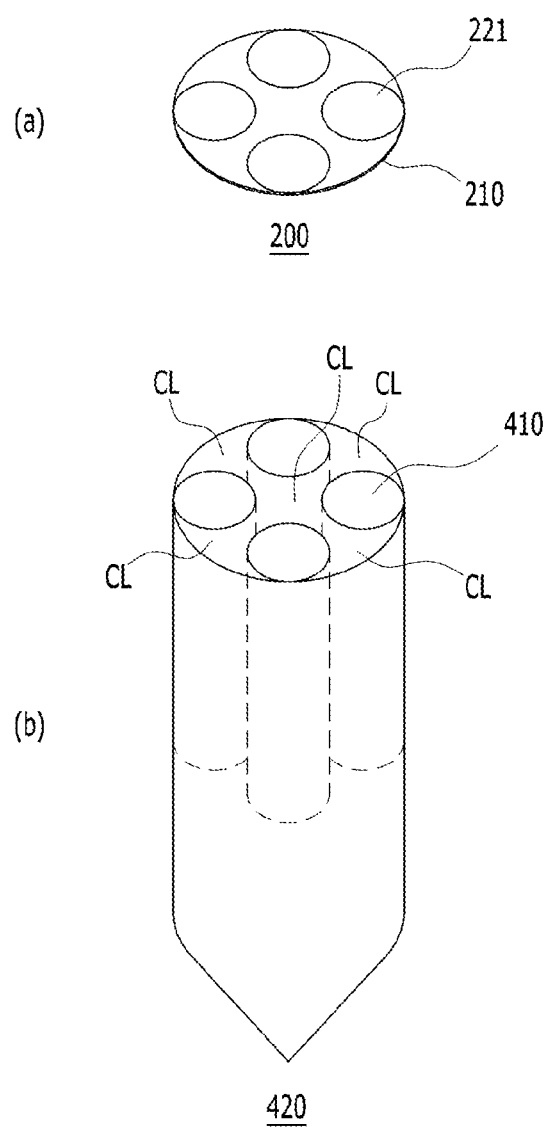
FIG. 6 is a bird's eye view of another shape control mold where a wire-shaped protrusion having four wires is formed in the manufacturing method according to the exemplary embodiment of the present invention, and a cross-sectional view of a microneedle manufactured by using the same.

Specifically, as shown in an example of FIG. 6, when a wire-shaped protrusion includes two or more wires, the two or more wires may each contact an edge of the opening area.

Specifically, FIG. 6(a) is a bird's eye view of an example of when the wire-shaped protrusion includes four wires 221, the shape control mold 200 is viewed from the protrusion direction of the wires 221, and illustrates each of the four wires 221 contact the edge of the opening area 211.

Thus, as shown in FIG. 6(b), a portion where the wire-shaped pore 410 of the microneedle 420 is located may have an open pore-shaped wire-shaped pore 410 having an opening formed on a side surface of the microneedle, may have a material axis CL at a center of the microneedle, and may also have a material axis CL in a length direction of the microneedle in an area where a wall surface between the surface of the microneedle 420 and the wire-shaped pore 410 is relatively thick.

The microneedle structure having the structure shown in FIG. 6(b) can assure strength that can endure an external force by the material axes CL, and all the wire-shape pores can be filled with the body fluid through the opened opening of the microneedle at the same time of insertion into the body such that the microneedle can be more promptly cut.

When the microneedle structure is manufactured by using the manufacturing method according to the exemplary embodiment of the present invention, a structure in which the wire-shaped pore of the microneedle structure not only penetrates the base portion of the wire but also penetrates the base layer that connects between the base portions of the wires such that the opening is formed in the base layer. Such a structure enables material supply into the pore (i.e., wire-shaped pore) of the microneedle structure from the outside during use of the microneedle structure.

Accordingly, for faster dissolution or decomposition, the solvent of the biocompatible polymer may be injected into the wire-shaped pore by applying the solvent of the biocompatible polymer to the base layer during use.

The wire-shaped protrusion of the shape control mold can satisfy the following Equation 3, and it is advantageous to satisfy Equation 3 in terms of strength assurance and rapid dissolution to prevent physical destruction during the insertion process by the material axes described above.

$$0.1 \leq A_{wire}/A_0 \leq 0.9 \tag{Equation 3}$$

In Equation 3, $A_{wire}$ denotes a total area of all wire cross-sections included in a protrusion, and $A_0$ denotes the area of an opening area.

Specifically, when the wire-shaped protrusion includes a single wire, a diameter of the wire may be a diameter in a case that a cross-section of a minor axis of a wire corresponds to 10% to 90% of a minor cross-section $A_0$ of the microneedle.

Unlike this, when the wire-shaped protrusion includes n wires (here, n is a natural number from 2 to 12), each wire has the same diameter in terms of securing the radial uniform mechanical properties of the manufactured microneedle, but may be a diameter of a case that a sum $\Sigma_{i=1}^{n} 4$, of a cross-section ($A_i$, I is a natural number from 1 to n) of a minor axis of each wire corresponds to 50% to 80% of the minor cross-section $A_0$ of the microneedle.

Figure 7:
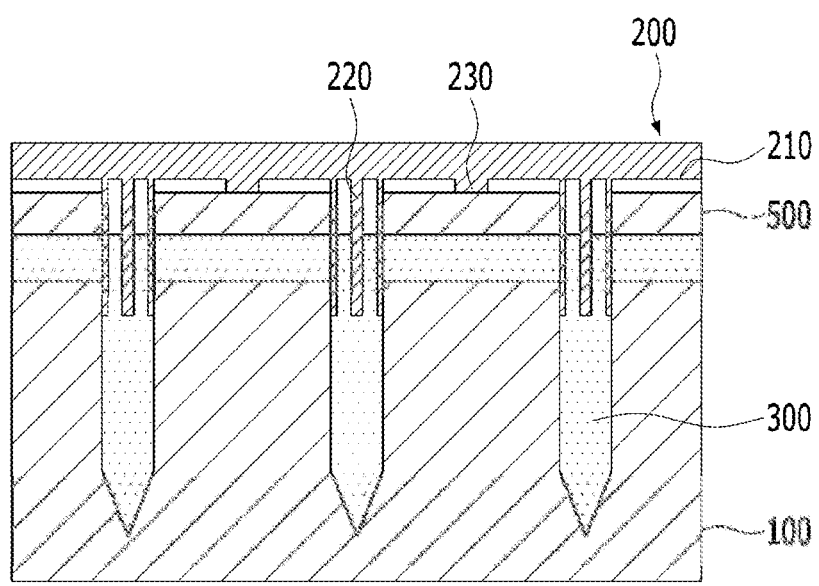
FIG. 7 is a cross-sectional view of the shape control mold that further includes a spacer in the manufacturing method according to the exemplary embodiment of the present invention.

FIG. 7 is a cross-sectional view of a shape control mold 200 that further includes a spacer 230 in the manufacturing method according to the exemplary embodiment of the present invention. As shown in the example of FIG. 7, the shape control mold 200 may further include a spacer 230 that forms an empty space between a flat panel 210 and an upper mold 500 on the same side of one side of the flat panel 210, in which the wire-shaped protrusion 220 is located.

The spacer 230 formed in the flat panel 210 may provide a path through which air when the wire-shaped protrusion 220 is charged into a polymer solution or by-products generated during curing (e.g., a vaporized solvent) is easily discharged by forming an empty space that is communicated with the outside (the air) between the flat panel 210 and the upper mold 500. A thickness of the spacer is sufficient as long as it can provide a stable vent, and as a practical example, a thickness of 100 μm to 10 mm is sufficient.

Figure 8:
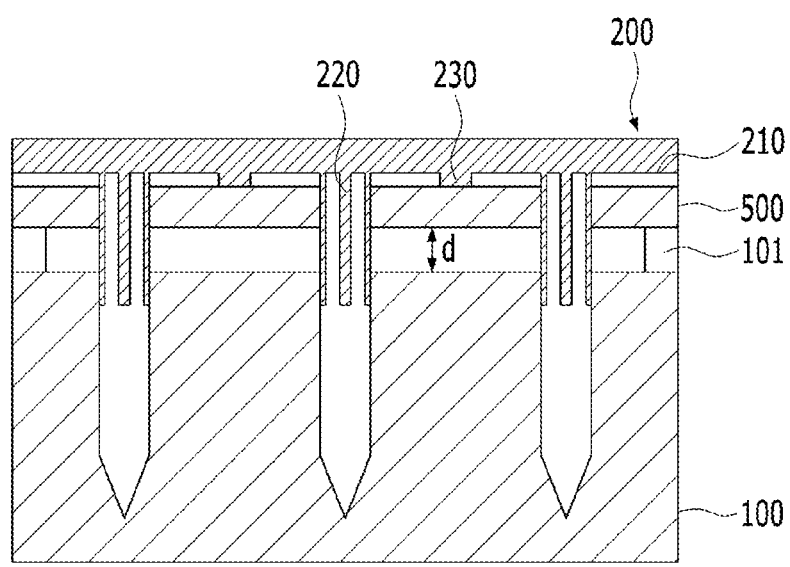
FIG. 8 is a cross-sectional view that illustrates a lower mold that includes an intaglio array, a shape control mold that includes an array of wire-shaped protrusions corresponding to the intaglio array, and an upper mold that includes an array of penetration-type pores corresponding to the intaglio array.

FIG. 8 is a cross-sectional view that illustrates a lower mold 100 that includes an intaglio array of two or more microneedle intaglios that are arranged apart from each other, a shape control mold 200 that includes an array of wire-shaped protrusions corresponding to the intaglio array, and an upper mold 500 that includes an array of penetration-type pores corresponding to the intaglio array. In this case, the expression "corresponding to the intaglio array" implies the same alignment and position as the microneedle intaglios that form the intaglio array.

As shown in the example of FIG. 8, in the manufacturing method according to the exemplary embodiment of the present invention, the lower mold 100 or the upper mold 500 may further include a separation member 101 that separates a lower surface of the upper mold 500 and a surface of the lower mold 100, in which the microneedle intaglio is formed, and which face each other.

As described above with reference to FIG. 2, the polymer solution may be injected into a separation space d formed by the separation member 101, and the polymer solution 300 injected into the separation space d may be converted into a base layer of a biocompatible polymer material that connects base portions between two or more microneedles by being cured.

As a size and a shape of the base layer are defined by the separation member 101, the separation member 101 may be formed in the shape of a closed loop, and the closed loop may have a designed size so as to be used as a single patch. Through this, the microneedle structure of the unit used as a single patch by the separation member 101 may be manufactured.

Unlike this, the separation member 101 may be formed in the shape of a closed loop that is located at an edge (i.e., an edge where the microneedle intaglio is not formed) of the lower mold 100 while surrounding the microneedle intaglio array. A large-sized microneedle structure can be manufactured by such a closed-loop shaped separation member.

In this case, a thickness of the separation member 101 may be appropriately adjusted in consideration of a thickness of the base layer formed of the biocompatible polymer material and connecting the base portions of the two or more microneedles. As a practical example, the thickness of the spacer 101 may be a level of 0.5 mm to 20 mm, but is not limited thereto.

In addition, the example shown in FIG. 8 is a case in which the separation member 101 is integrally formed with the lower mold 100, but this is not restrictive, and the separation member 101 may be integrally formed with the upper mold 500.

The manufacturing method according to the exemplary embodiment of the present invention may further include a separation mold 600 that corresponds to the separation member described above with reference to FIG. 8. That is, the example shown in FIG. 8 is a case in which the separation member is integrally formed with the upper or lower mold, but a separation mold 600 that is individually formed with the lower mold and the upper mold may be used.

Figure 9:
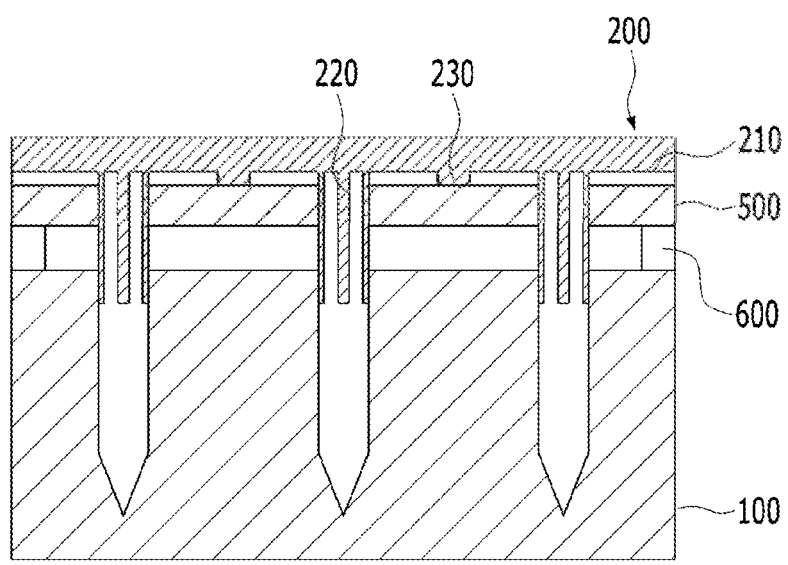
FIG. 9 is an exploded perspective view of the lower mold, the upper mold, and a separation mold in the manufacturing method according to the exemplary embodiment of the present invention.

As shown in FIG. 9, the separation mold 600 is located between a lower mold 100 and an upper mold 500 for separation therebetween. Similar to the separation member 101, the separation mold 600 may also be a closed loop having a constant thickness (a thickness in a vertical direction), and a size and a shape of a base layer formed of a biocompatible polymer material and connecting base portions of two or more microneedles can be controlled by a size and a shape of the separation mold 600.

As shown in FIG. 9, when the separation mold 600 separated from the upper mold 500 and the lower mold 100 is used, different types of microneedle structures can be manufactured by simply using a separation mold 600 having a size and a shape that are different from those of the upper mold 500 and the lower mold 100 even through the upper mold 500 and the lower mold 100 are the same.

That is, a microneedle structure having various sizes and shapes that are in accordance with usage of a patch that includes the microneedle structure through a single process for adjusting a shape and a size of the separation mold 600 can be provided.

As described above, in the manufacturing method according to the embodiment of the present invention, an area where the microneedle is cut may be strictly specified to be between the opening (opening in the lower mold) of the microneedle intaglio and a position where one end of the wire-shaped protrusion is fixed.

More specifically, an area where the microneedle is cut may be more strictly specified into an area to one end of the wire-type protrusion while zeroing the opening portion (the base portion of the microneedle) of the microneedle intaglio, excluding an area where body fluid is not formed and where microneedle dissolution or decomposition does not occur by body fluids such as the stratum corneum or a transparent layer.

As the area in which the microneedle is cut is strictly defined, the manufacturing method according to the exemplary embodiment of the present invention allows the microneedle to contain only the drug in the lower portion of the cutting area so that a strictly designed dose of drug can be injected into the body.

Figure 10:
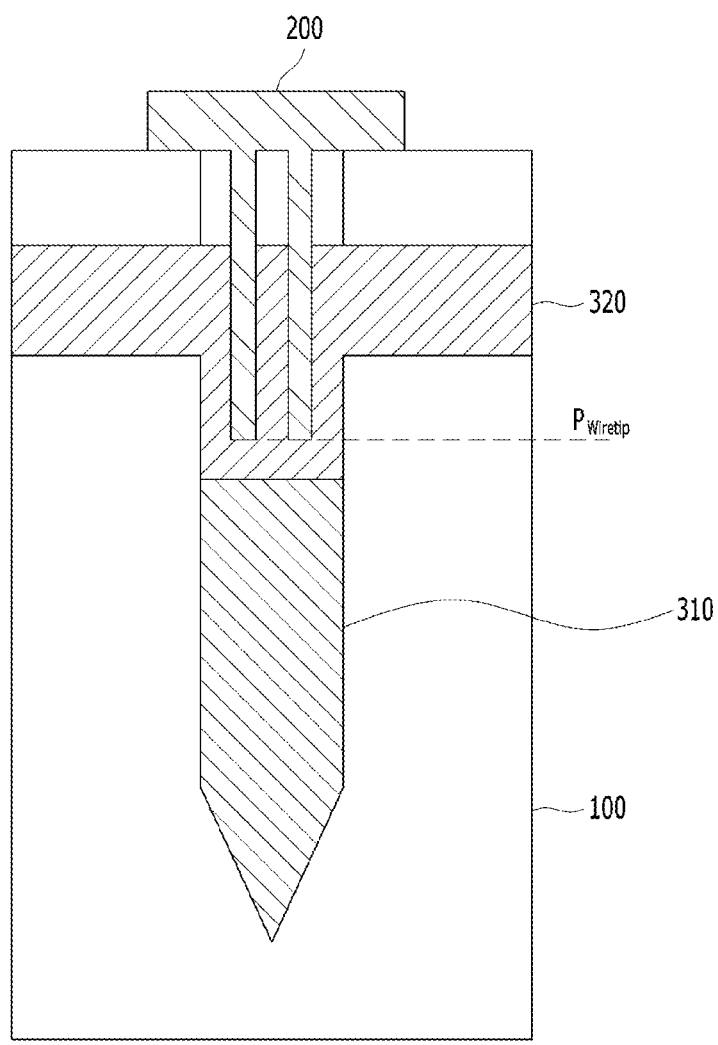
FIG. 10 is a process diagram of a polymer solution injection process in the manufacturing method according to the exemplary embodiment of the present invention.

Specifically, as shown in an example of FIG. 10, the injection of the polymer solution may include: a2-1) injecting a first polymer solution 300 that contains a first biocompatible polymer and a drug into the microneedle intaglio 110, while locating a liquid level of the first polymer solution 300 in a lower portion of $P_{wiretip}$; and a2-2) injecting a second polymer solution 300 that contains a second biocompatible polymer to fill a space of the microneedle intaglio 110 above the liquid level of the first polymer solution 300.

Accordingly, when the microneedle structure is used, while the microneedle is cut in a short time, only the portion remaining in the body contains the drug such that the drug of the exactly designed dose can be stably supplied to the body.

The drug contained in the first polymer solution or the polymer solution may imply biochemical materials or drugs to treat diseases, including: a cell material; a genetic material; metabolites of organisms; an organic material that affects a biological material synthesis process, a biological material transport process, or a biological signal transmission process. That is, the drug is a material used for the treatment of a disease occurring in an animal including a human and cannot be interpreted limitedly, and may include a material that can be used for the purpose of preventing, diagnosing, or treating a disease occurring in an animal including a human.

The first biocompatible polymer and the second biocompatible polymer may be homogeneous or heterogeneous biocompatible polymers, but may advantageously be different polymers.

As described above, the first polymer solution and the second polymer solution can be used to design the material of the microneedle remaining in the body and a material of the microneedle of the area being cut.

Accordingly, the microneedle area (i.e., below $P_{wiretip}$) remaining in the body may prioritize stability in the body above all due to the cutting of the microneedle, and a microneedle area located above $P_{wiretip}$ may prioritize prompt cutting of the microneedle by dissolution or decomposition.

Accordingly, the first biocompatible polymer may be a biodegradable polymer having excellent stability in the body and that is capable of supplying a drug for a long time, and the second biocompatible polymer may be a water-soluble polymer (biosoluble polymer) that is capable of rapid dissolution.

Dissolution removal speed of water-soluble polymers (biosoluble polymers) is significantly faster than biodegradable polymers, and furthermore, it is advantageous to supply water to wire-shaped pores from the outside, thereby further promoting dissolution removal.

In the manufacturing method according to the exemplary embodiment of the present invention, described above with reference to FIG. 1 to FIG. 10, the lower mold 100 is illustrated as a single mold, but the present invention is not limited thereto.

Figure 11:
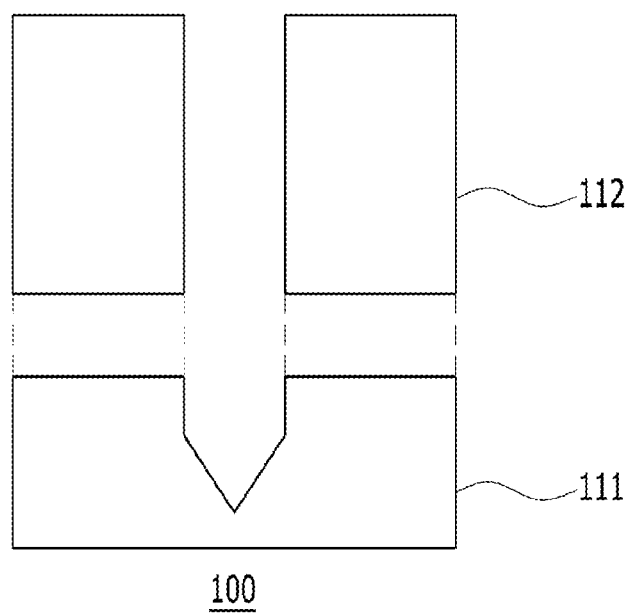
FIG. 11 is a cross-sectional view of a detailed example of the lower mold in the manufacturing method according to the exemplary embodiment of the present invention.

Specifically, as shown in an example of FIG. 11, a lower mold 100 may include a first lower mold 111 and a second lower mold 112, the first lower mold 111 may include a first intaglio area corresponding to the tip of the microneedle, and the second lower mold 112 may include a second intaglio area corresponding to the pillar of the microneedle, including a base portion of the microneedle.

The first lower mold 111 and the second lower mold 112 may be coupled such that the first intaglio area and the second intaglio area have concentric structures, and the intaglio of one microneedle may be formed by coupling the first intaglio area and the second intaglio area.

As shown in FIG. 11, when the intaglio of the microneedle is formed by coupling two or more molds, a microneedle structure having various lengths may be manufactured by simply replacing a second lower mold that is coupled with a first lower mold, and a microneedle structure having a tip of various shapes can be manufactured by simply replacing the first lower mold coupled with the second lower mold such that design flexibility and design freedom can be significantly improved at a low cost.

In the manufacturing method according to the exemplary embodiment of the present invention, described with reference to FIG. 1 to FIG. 11, a functional coating layer may be formed at the surface of the mold. Specifically, at least the microneedle intaglio surface of the lower mold, advantageously the intaglio surface of the lower mold and a lower mold opposing surface of the upper mold, more advantageously the intaglio surface of the lower mold, the lower mold opposing surface of the upper mold, and a surface of a wire-shaped protrusion of the shape control mold, may be formed with a functional coating layer.

The functional coating layer may be a material layer that allows easier detachment by relieving the binding force between the mold and the cured polymer solution when the microneedle structure is detached from the mold after curing of the injected polymer solution.

In detail, the functional coating layer may be a hydrophobic coating layer, and the hydrophobic coating layer may be a coating layer of a hydrophobic material having a contact angle of 90° or more and substantially 120° or more.

For example, the hydrophobic coating layer may be a hydrophobic resin layer, and one or more may be selected from fluorine resin, acryl-based resin, urethane-based resin, polyester resin, vinyl resin, and silicone resin as the hydrophobic resin.

More specifically, in one more specific example, the hydrophobic resin may be a chemically and optically stable fluorine resin that provides a hydrophobic to a super hydrophobic surface characteristic. As an example of fluorine resin, polytetrafluoroethylene, polyvinylidene fluoride, polyvinyl fluoride, a polychlorotrifluoroethylene, a tetrafluoroethylene-hexafluoropropylene copolymer, an ethylene-tetrafluoroethylene copolymer, an ethylene chlorotrifluoroethylene copolymer, a tetrafluoroethylene perfluoroalkylvinylether copolymer, a perfluorocyclopolymer, a vinyl etherfluoroolefin copolymer, a vinyl ester fluoroolefin copolymer, a tetrafluoroethylene vinyl ether copolymer, a chlorotrifluoroethylene vinyl ether copolymer, a tetrafluoroethylene urethane binder, a tetrafluoroethylene epoxy binder, a tetrafluoroethyleneacryl binder, a tetrafluoroethylene melamine binder, and the like may be included, and tetrafluoroethylene, which can stably maintain high hydrophobicity (water repellency) having a contact angle of higher than 120°, is more advantageous. Also, as an example of a hydrophobic material having oleophobicity with hydrophobicity, fluorinated alkylsilanes may be included, alkyltrihalo- or trialkoxy-silane, etc., of which an alkyl group contains at least one end which has a perfluoro functional group, may be included, or a mixture of an alkoxysilane having a perfluoro functional group at the end and a halosilane having a perfluoro functional group at the end may be included, but the present invention is not limited by the material of the coating layer.

In the manufacturing method according to an exemplary embodiment of the present invention, two molds (e.g., an upper mold and a shape control mold, a lower mold and an upper mold, a first lower mold and a second lower mold, a lower mold and a separation mold, and a separation mold and an upper mold) that are coupled adjacent to each other may be combined with each other for protrusions and depressions.

As a specific and non-limiting example, a guide protrusion may be located on a coupling surface of one mold of two coupled molds, while being adjacent to each other, and a guide groove may be located on a coupling surface of the other mold.

As the guide protrusion and the guide groove are unevenly coupled with each other, the two molds adjacent to each other can be physically stably coupled and may be precisely combined into the designed position.

However, the present invention is not limited by the specific method of coupling between molds (e.g., uneven coupling), and any known means of binding and detaching the two objects reversibly to have a designed positional relationship may be used.

The present invention includes a microneedle structure manufacturing apparatus, and the apparatus may be an apparatus used in the above-described manufacturing method.

The microneedle structure manufacturing apparatus according the present invention includes a lower mold including a microneedle intaglio and is coupled with the lower mold such that one end of the protrusion is inserted into the microneedle intaglio, and an injection portion that injects a polymer solution into the microneedle intaglio of the lower mold.

In this case, any typical injection device used to inject a designed amount of liquid into a designed position is applicable as the injection portion. Specifically, for example, the injection portion may include injection means that is connected with a reservoir where a polymer solution is stored through a pump is provided to be movable in three axes (x, y, and z) that are perpendicular to each other.

Alternatively, the injection portion may include a three-axis movable stage where an injection means connected with the reservoir where the polymer solution is stored through a pump and a mold including a lower mold, and the three axes are perpendicular to each other, but the present invention is not limited thereto.

Molds including a lower mold and a shape control mold, and an upper mold and a separation mold, which will be described later, may have a structure that is similar to or the same as those described in the manufacturing method of the microneedle structure.

Specifically, the shape control mold may planarize an area, and a protrusion of the shape control mold includes a wire, which may be disposed in an opening area, that is, a flat area corresponding to an opening of the microneedle intaglio.

In addition, the protrusion may include one to twelve wires. When the protrusion includes one wire, the protrusion may be located at a center of the opening area, and when the protrusion includes two or more wires, the two or more wires may be located to surround the center of the opening area while satisfying Equation 2.

$$\theta = 360°/n \quad \text{(Equation 2)}$$

Herein, θ denotes an angle between two wires that neighbor each other with reference to a center of the opening area, and n is a natural number from 1 to 12, which corresponds to the number of wires included in the protrusion portion.

In addition, when the protrusion portion includes two or more wires, the wires of the protrusion may be located while contacting the edge of the opening area, or may contact neighboring wires.

The protrusion of the shape control mold may satisfy Equation 3.

$$0.1 \leq A_{wire}/A_0 \leq 0.9 \quad \text{(Equation 3)}$$

In Equation 3, $A_{wire}$ is a total wire area, which is a sum of all wire cross-sections included in the protrusion, and $A_0$ is the area of the opening area.

Similar to the above-described manufacturing method, the microneedle structure manufacturing apparatus may further include an upper mold where a penetration-type pore is formed. The upper mold may be be coupled with the lower mold such that the penetration-type pore is located above the microneedle intaglio opening, and the protrusion of the shape control mold is positioned on the upper mold such that one end of the protrusion can be located inside the microneedle intaglio through the penetration-type pore of the upper mold.

In addition, the shape control mold may further include a spacer that forms an empty space (separation space) between the flat panel and the upper mold on on a side that is the same as one side of the flat panel in which the protrusion is located, and the separation space formed by the spacer enables formation of a flat-shaped base layer extends from the base portion of the microneedle.

In addition, since the protrusion of the shape control mold is inserted into the microneedle intaglio through the penetration-type pore of the upper mold, wire-type pores that penetrate into the base layer, which becomes a surface layer in contact with the external atmosphere, and extend into the microneedle, may be formed in use of a patch including the microneedle structure. Therefore, the wire-shaped pores of the microneedle may be maintained to be opened during use of the patch including the microneedle structure.

In addition, when the lower mold includes an intaglio array in which two or more microneedle intaglios are arranged at a distance from each other, and the upper mold includes a penetration-type pore array that corresponds to the intaglio array, a microneedle structure in which base portions of a plurality of needles are fixed to a single base layer can be manufactured.

When the lower mold includes the intaglio array and the upper mold include the penetration-type pore array, the shape control mold may include an array of wire-type protrusion(s) corresponding to the intaglio array.

The microneedle structure manufacturing apparatus according to the exemplary embodiment of the present invention may further include a separation mold that is located between the lower mold and the upper mold for separation therebetween.

However, similar to the above-described manufacturing method, the separation mold may be integrally formed with the lower mold or the upper mold rather than being provided individually from the upper mold and the lower mold.

In the microneedle structure manufacturing apparatus according to the exemplary embodiment of the present invention, the lower mold may include a first lower mold that includes a first intaglio area corresponding to a tip of the microneedle and a second lower mold that includes a second intaglio area corresponding to a pillar of the microneedle.

That is, the first lower mold and the second lower mold are coupled to enable the first intaglio area of the first lower mold and the second intaglio area of the second lower mold to communicate with each other such that the lower mold can be formed.

The lower mold having such a multi-layered structure is advantageous since it enables manufacturing of a microneedle structure having various sizes or shapes by only simply replacing a mold (e.g., the first lower mold or the second lower mold).

A functional coating layer may be formed in a surface of the mold. Specifically, at least the microneedle intaglio surface of the lower mold, advantageously the intaglio surface of the lower mold and a lower mold opposing surface of the upper mold, more advantageously the intaglio surface of the lower mold, the lower mold opposing surface of the upper mold, and a surface of a wire-shaped protrusion of the shape control mold, may be formed with a functional coating layer.

Specifically, the functional coating layer may be a hydrophobic coating layer and the hydrophobic coating layer may be a hydrophobic resin layer, and one or more may be selected as the hydrophobic resin from a fluorine resin, an acryl-based resin, a urethane-based resin, a polyester resin, a vinyl resin, and a silicone resin.

The present invention includes a microneedle structure manufactured by using the above-described manufacturing method.

Figure 12:
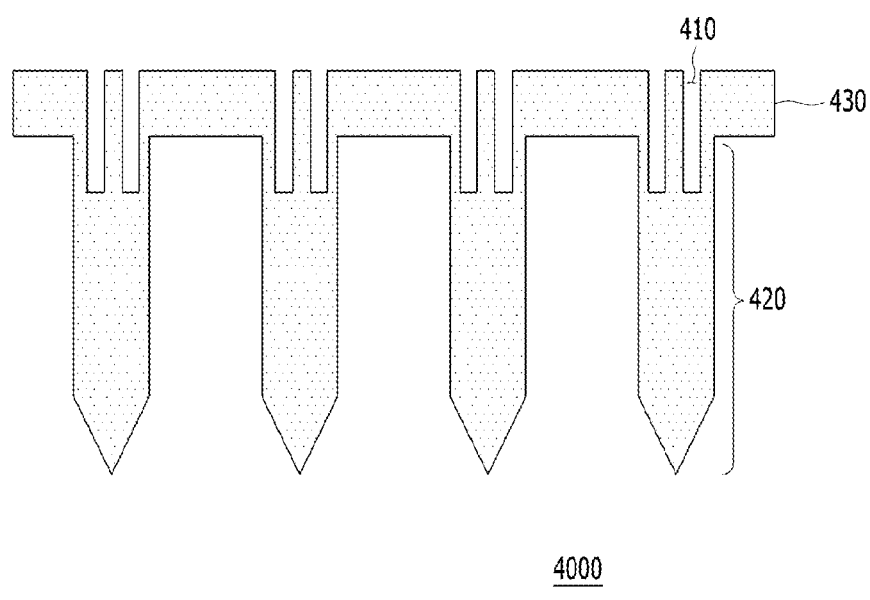
FIG. 12 is a cross-sectional view illustrating a cross-section of a microneedle structure according to an exemplary embodiment of the present invention.

FIG. 12 is a cross-sectional view illustrating a cross-section of a microneedle structure according to the present invention, and a microneedle structure 4000 includes a base layer 430, which is a flat layer, and microneedles 420, which are disposed on one side of the base layer 430 and formed of a biocompatible polymer material, and each microneedle 420 includes a wire-shape pore 410 that extends in a tip direction of the microneedle from the base portion of the microneedle while penetrating the base layer 430 such that one end of the wire-shaped pore 410 is located inside the microneedle 420.

In this case, the base layer 430 may connect base portions of two or more microneedles 420, and may be physically integrally formed with the microneedle 420. When the base layer 430 is physically integrally formed with the microneedle 420, the base layer 430 may also be formed of a biocompatible polymer material.

The wire-shaped pore 410 may satisfy Equation 4, and when the microneedle structure is in use, cutting may be carried out in an area specified from the base portion of the microneedle to one end of the wire-shaped pore 410.

$$0.1L_1 \leq E_{tip} \leq 0.9L_1 \quad \text{(Equation 4)}$$

In Equation 4, $L_1$ denotes a length of the microneedle, and $E_{tip}$ denotes a position of one end of the wire-shaped pore while zeroing the tip of the microneedle That is, $E_{tip}$ implies a distance from the microneedle tip to one end of the wire-shaped pore.

In the microneedle structure according to the exemplary embodiment of the present invention, the microneedle may include two to twelve wire-shaped pores.

FIG. 13(a) is a transmissive perspective view illustrating an example in which the microneedle 420 includes one wire-shaped pore 410, FIG. 13(b) is a transmissive perspective view illustrating an example in which the microneedle 420 includes three wire-shaped pores 410, FIG. 13(c) is a transmissive perspective view illustrating an example in which the microneedle 420 includes four wire-shaped pores 410, and FIG. 13(d) is a transmissive perspective view illustrating an example in which the microneedle 420 includes six wire-shaped pores 410, and a minor cross-section is illustrated together for clarity.

Figure 13:
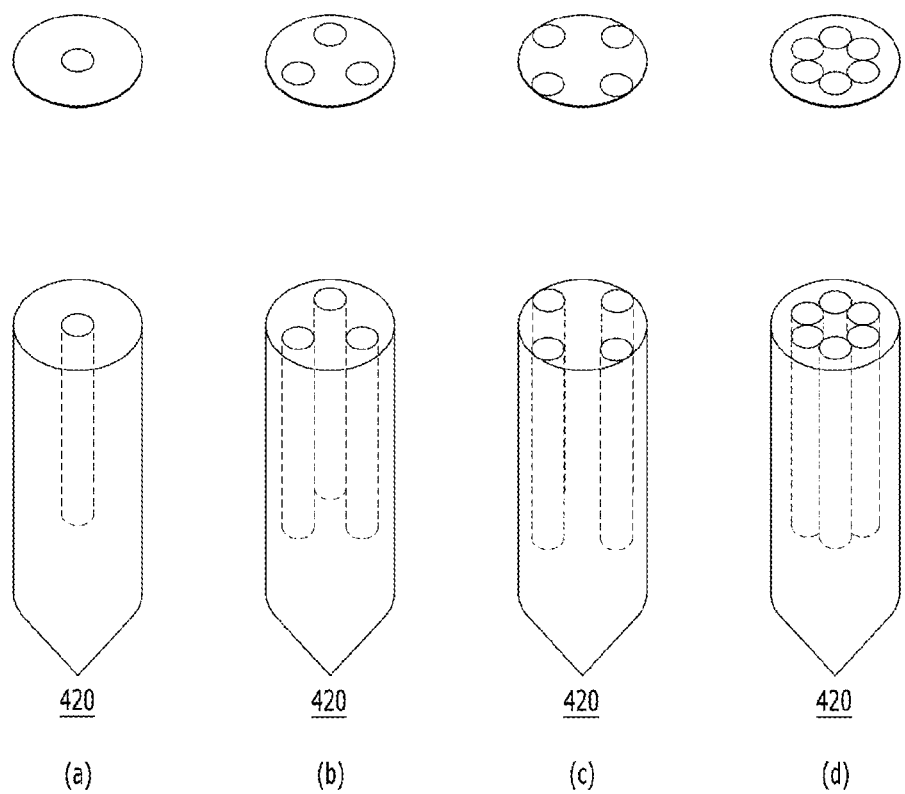
FIG. 13 is a transmissive perspective view illustrating the cross-section of the microneedle structure according to the exemplary embodiment of the present invention.

As shown in the examples of FIG. 13, when the microneedle 420 includes one wire-shaped pore 410, the wire-shaped pore 410 may have a concentric structure about the central axis of the length direction of the microneedle.

Unlike this, when the microneedle 420 includes two to twelve, specifically three to six, wire-shaped pores 410, the wire-shaped pores 410 may be arranged to surround the central axis of the length direction of the microneedle.

Specifically, as in the examples shown in FIG. 13, when the microneedle 420 includes two or more wire-shaped pores 410 and when a wire-shaped protrusion of each wire-shaped pore 410 includes two or more wires, the two or more wires may satisfy the following Equation 6. That is, when the wire-shaped protrusion includes two or more wires 221, the wires may be regularly positioned to surround the center of an opening region 211.

$$\theta' = 360°/n \quad \text{(Equation 6)}$$

Herein, $\theta'$ denotes an angle (°) between two wire-shaped pores that neighbor each other with reference to a center of the base portion of the microneedle, and n denotes a natural number from 2 to 12, which is the number of wire-shaped pores formed in the microneedle.

In this case, the angle of the two wire-shaped pores that neighbor each other is an angle between two line segments connecting the center of each wire-shaped pore and the center of the microneedle base portion on an imaginary plane including the microneedle base portion.

As in the examples shown in FIG. 13, when the number of the wire-shaped pores 410 is three, an angle between neighboring wires may be 120°, when the number is 4, the angle may be 90°, and when the number is 6, the angle may be 60°.

As the wire-shaped pores are located regularly around the microneedle's central axis that connects the center of the microneedle's base portion and the microneedle tip, a material axis that can support physical forces from the needle tip to the base portion of the microneedle may be formed, and when the microneedle structure is in use, it is possible to prevent the external force such as penetration pressure from being concentrated locally in some regions.

As shown in the example of FIG. 13(b), the wire-shaped pore 410 is regularly positioned to surround the central axis of the base portion of the microneedle 420 that connects the center of the base portion of the microneedle 420 and the microneedle tip, but the wire-shaped pore 410 may be positioned inside the microneedle 420 while being paced apart from each other.

Unlike this, as shown in the example of FIG. 13(c), the wire-shaped pore 410 is regularly positioned to surround the central axis of the base portion of the microneedle 420 that connects the center of the base portion of the microneedle 420 and the microneedle tip, but the wire-shaped pore 410 may be in contact with the surface of the microneedle 420 so that the outside of the microneedle 420 and the wire-shaped pore 410 communicate with each other. That is, in such a case, together with an opening through the base portion and the base layer of the microneedle, an opening may also be formed in a side surface of the microneedle.

Unlike this, as shown in the example of FIG. 13(d), the wire-shaped pores 410 are regularly positioned to surround the central axis of the base portion of the microneedle 420 that connects the center of the bases portion of the microneedle 420 and the microneedle tip, but adjacent wire-shaped pores 410 may have a structure in which they communication with each while being in contact with each other.

In the microneedle structure according to the exemplary embodiment of the present invention, the microneedle may satisfy the following Equation 5.

$$0.1 \leq A_{empty}/A_1 \leq 0.9 \quad \text{(Equation 2)}$$

In Equation 5, $A_{empty}$ denotes a total empty space area of cross-sections of all wire-shaped pores included in a microneedle, and $A_1$ denotes a cross-section of the microneedle. As Equation 5 is satisfied, the microneedle may be be promptly cut by dissolving or decomposing a wire-shaped pore wall while ensuring the strength such that the microneedle does not break down while penetrating the biological barrier.

In the microneedle structure according to the exemplary embodiment of the present invention, a first region, which is a region below one end of the wire-shaped pore from the microneedle tip, may contain a first biocompatible polymer and drug, and the remaining microneedle region (i.e., a second region) except the first region may contain a second biocompatible polymer. In this case, the biocompatible polymers in the first region and the second region may be different from each other, and in terms of stability and drug delivery speed control, it is advantageous for the first region contains biodegradable polymers and the second region to contain biosoluble polymers (water-soluble polymers).

The present invention includes a method for using a patch that includes the above-described microneedle structure.

Figure 14:
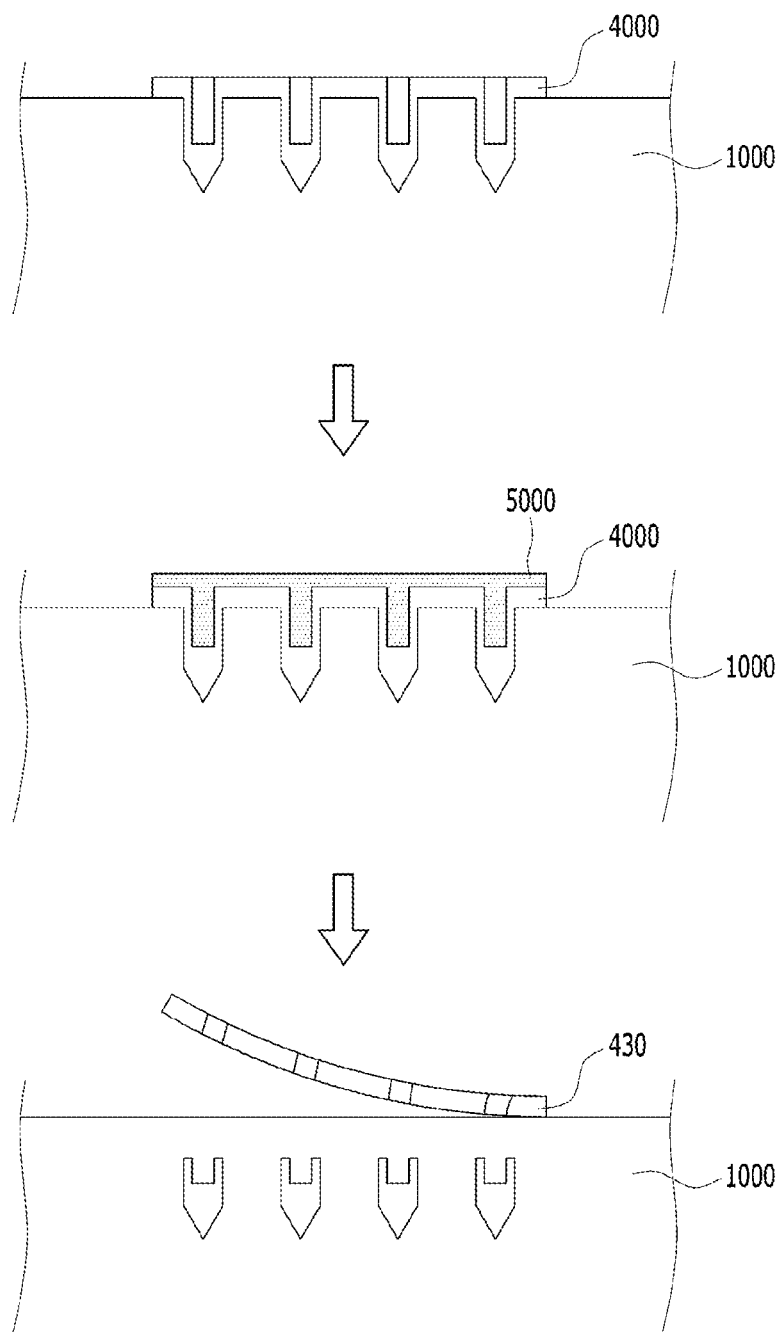
FIG. 14 is a process diagram of a patch using method according to the present invention.

FIG. 14 is a process diagram of a patch using method according to the present invention. As exemplarily shown in FIG. 14, a patch using method includes attaching a patch that includes the above-described microneedle structure 4000 to an attachment target 1000, injecting a solvent 5000 that dissolves a biocompatible polymer to a wire-shaped pore by coating the solvent 5000 to the base layer 430 of the microneedle structure 4000, and separating the base layer 430 from the attachment target 1000.

In the attaching of the patch including the microneedle structure 4000 to the attachment target 1000, when the microneedle structure includes a single wire-shaped pore, a tube-shaped material axis having a uniform thickness is formed along the outer circumference of the microneedle such that physical strength that can withstand penetration pressure can be assured.

In addition, in the attaching of the patch including the microneedle structure 4000 to the attachment target 1000, when the microneedle structure includes two or more wire-shaped pores, a material axis that continuously extends from the center of the microneedle base portion to the tip of the microneedle and material axes that act as a support axis to withstand external pressure while forming a regular radial cross-section (microneedle cross-section) by the pore walls of the wire-shaped pores, and thus excellent physical strength can be assured.

As the microneedle structure is designed, a stable strength that can withstand penetration pressure can be provided, thereby preventing damage to the microneedle during the attachment process, and the microneedle can be cut as the relatively thin pore wall of the wire-shaped pore is dissolved or decomposed such that attachment time (utilization time) can be significantly shortened.

Furthermore, as the wire-shaped pore formed in the microneedle in the microneedle structure have opening in the base layer, dissolution or decomposition speed of the pore wall of the wire-shaped pore can be significantly improved by applying a solvent (e.g., water) that dissolves the biocompatible polymer from the outside.

The present invention as described above has been described through specific matters and limited embodiments and drawings, but this is only provided to help a more general understanding of the present invention. The present invention is not limited to the above embodiments, and various modifications and variations are possible to those skilled in the art from this description.

Thus, this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

The invention claimed is:

1. A microneedle structure manufacturing method comprising:
   a) injecting a polymer solution containing a biocompatible polymer into a lower mold that includes a microneedle intaglio;
   b) coupling a shape control mold to the lower mold to impregnate one end of a protrusion included in the shape control mold into the biocompatible polymer solution injected into the microneedle intaglio; and
   c) curing the polymer solution and removing a mold that includes the lower mold and the shape control mold,
   wherein
   the a) comprises:
   a1) combining an upper mold including through-holes to be spaced apart from an upper portion of the lower mold, while disposing a penetration-type pore apart from an upper portion of the microneedle intaglio; and
   a2) injecting the polymer solution to fill at least a part of a separation space between the upper mold and the lower mold while filling the microneedle intaglio, and
   in the b), one end of the protrusion is impregnated into the biocompatible polymer solution filled in the microneedle intaglio through the penetration-type pore.

2. The microneedle structure manufacturing method of claim 1, wherein, in the b), the shape control mold is coupled to the lower mold to satisfy Equation 1:

$$0.1L_0 \leq P_{wiretip} \leq 0.9L_0, \quad \text{(Equation 1)}$$

wherein $L_0$ denotes a length of the microneedle intaglio, and $P_{wiretip}$ denotes a position of one end of the protrusion when a lowest point of the microneedle intaglio is zeroed.

3. The microneedle structure manufacturing method of claim 2, wherein the a2) comprises:
   a2-1) injecting a first polymer solution that contains a first biocompatible polymer and a drug into the microneedle intaglio, while locating a liquid level of the first polymer solution in a lower portion of the $P_{wiretip}$; and
   a2-2) injecting a second polymer solution that contains a second biocompatible polymer to fill a space of the microneedle intaglio above the liquid level of the first polymer solution.

4. The microneedle structure manufacturing method of claim 1, wherein
   the shape control mold further comprises a flat panel, and
   in the b), the protrusion is located only in an opening area, which is a flat panel area corresponding to an opening of the microneedle intaglio in the flat panel of the shape control mold, and the protrusion comprises one to twelve wires.

5. The microneedle structure manufacturing method of claim 4, wherein
   when the protrusion comprises one wire, the wire is located at a center of the opening area, and when the protrusion comprises two or more wires, the wires are located to satisfy Equation 2:

$$\theta = 360°/n, \quad \text{(Equation 2)}$$

wherein $\theta$ denotes an angle (°) between two wires neighboring each other with reference to the center of the opening area, and n denotes a natural number from 2 to 12, which is the number of wires.

6. A microneedle structure manufacturing apparatus comprising:
   a lower mold that includes a microneedle intaglio;
   a shape control mold that includes a protrusion, and is coupled with the lower mold to impregnate one end of the protrusion into the microneedle intaglio; and
   an injection portion that injects a polymer solution into the microneedle intaglio of the lower mold,
   wherein the shape control mold further comprises a flat panel, and
   the protrusion comprises one to twelve wires that are located in an opening area, which is a flat area corresponding to an opening of the microneedle, and when the protrusion includes one wire, the protrusion is located at a center of the opening area, while when the protrusion includes two or more wires, Equation 2 is satisfied:

$$\theta = 360°/n,\quad \text{(Equation 2)}$$

wherein θ denotes an angle (°) between two wires neighboring each other with reference to the center of the opening area, and n denotes a natural number from 2 to 12, which is the number of wires.

7. The microneedle structure manufacturing apparatus of claim 6, wherein the protrusion comprises two or more wires, and the two or more wires contact an edge of the opening area or neighboring wires contact each other.

8. The microneedle structure manufacturing apparatus of claim 6, wherein the protrusion satisfies Equation 3:

$$0.1 \leq A_{wire}/A_0 \leq 0.9,\quad \text{(Equation 2)}$$

wherein $A_{wire}$ denotes a total area of all wire cross-sections included in a protrusion, and $A_0$ denotes an area of an opening area.

9. The microneedle structure manufacturing apparatus of claim 6, further comprising an upper mold where a penetration-type pore is formed,
wherein the upper mold is coupled with the lower mold such that the penetration-type pore is located above an opening of the microneedle intaglio, and
the shape control mold further comprises a spacer that forms an empty space between the flat panel and the upper mold on a side that is the same as one side of the flat plane where the protrusion is located.

10. The microneedle structure manufacturing apparatus of claim 9, further comprising a separation mold that separates the upper mold and the lower mold while being disposed between the lower mold and the upper mold.

11. The microneedle structure manufacturing apparatus of claim 6, wherein the lower mold comprises a first lower mold that includes a first intaglio area that corresponds to a tip of the microneedle and a second lower mold that includes a second intaglio area that corresponds to a base portion and a pillar of the microneedle.

12. A microneedle structure comprising:
a base layer, which is a flat layer; and
a microneedle that is formed of a biocompatible polymer material and located on one side of the base layer,
wherein the microneedle comprises a pore that extends in a direction of a tip of the microneedle while penetrating the base layer such that one end of the pore is located inside the microneedle,
wherein the pore is two to twelve wire-shaped pores, and the wire-shaped pores are arranged to surround a central axis of a length direction of the microneedle.

13. The microneedle structure of claim 12, wherein the wire-shaped pores that are adjacent to each other communicate with each other while being in contact with each other.

14. The microneedle structure of claim 12, wherein the microneedle further comprises a second pore connecting a surface of the microneedle to at least one of the wire-shaped pores such that the at least one of the wire-shaped pores and an outside of the microneedle communicate with each other.

15. The microneedle structure of claim 12, wherein the pore satisfies Equation 4:

$$0.1 L_1 \leq E_{tip} \leq 0.9 L_1,\quad \text{(Equation 4)}$$

wherein $L_1$ denotes a length of the microneedle, and $E_{tip}$ denotes a position of one end of the wire-shaped pore while zeroing the tip of the microneedle, and
wherein the microneedle satisfies Equation 5:

$$0.1 \leq A_{empty}/A_1 \leq 0.9,\quad \text{(Equation 5)}$$

wherein $A_{empty}$ denotes a total empty space area of cross-sections of all wire-shaped pores included in the microneedle, and $A_1$ denotes a cross-section of the microneedle,
wherein a first area, which is an area from the tip of the microneedle to below one end of the wire-shaped pore, contains a first biocompatible polymer and a biochemical material, and other areas excluding the first area in the microneedle contain a second biocompatible polymer, and
wherein the first biocompatible polymer contains a biodegradable polymer and the second biocompatible polymer contains a biosoluble polymer.

* * * * *